(12) United States Patent
Bernard et al.

(10) Patent No.: US 7,019,000 B1
(45) Date of Patent: Mar. 28, 2006

(54) METHOD OF TREATING A DISEASE CONDITION CAUSED OR EXACERBATED BY AN HPV

(75) Inventors: Hans-Ulrich Bernard, Singapore (SG); Yee Joo Tan, Singapore (SG); Walter Beerheide, Singapore (SG); Anthony Eugene Ting, Singapore (SG); Mui Mui Sim, Singapore (SG)

(73) Assignee: Institute of Molecular & Cell Biology, Singapore (SG)

( * ) Notice: Subject to any disclaimer, the term of this patent is extended or adjusted under 35 U.S.C. 154(b) by 0 days.

(21) Appl. No.: 09/763,616

(22) PCT Filed: Sep. 3, 1999

(86) PCT No.: PCT/AU99/00724

§ 371 (c)(1),
(2), (4) Date: May 16, 2001

(87) PCT Pub. No.: WO00/14063

PCT Pub. Date: Mar. 16, 2000

(30) Foreign Application Priority Data

Sep. 4, 1998 (AU) .................................... PP5733
Jul. 15, 1999 (AU) .................................... PQ1645

(51) Int. Cl.
*A61K 31/415* (2006.01)
*A61K 31/54* (2006.01)
*C07D 417/04* (2006.01)

(52) U.S. Cl. .................................................. 514/227.8
(58) Field of Classification Search ............. 514/227.8
See application file for complete search history.

(56) References Cited

FOREIGN PATENT DOCUMENTS

EP 562750 9/1993
WO WO 96/09406 3/1996

OTHER PUBLICATIONS

Sherman et al., Virology 237: 296-306, 1997.
Chen et al., Science 269: 529-531, 1995.
Tong et al., Proc. Natl. Acad. Sci. USA 94: 4412-4417, 1997.
Sedman et al., J. Virol. 65: 4860-4866, 1991.
Lamberti et al., EMBO J. 9: 1907-1913, 1990.
Etscheid et al., Virology 205: 583-585, 1994.
Klingelhutz et al., Nature 380: 79-82, 1996.
Myers and Androphy, The E6 protein, pp III-47-III-57, 1995.
Grossman et al., Oncogene 4: 1089-1093, 1989.
Kanada et al., Virology 185: 536-543, 1991.
Dsouza et al., Trends in Genetics 13: 497-498, 1997.
Chan et al., Virol. 69: 3074-3083, 1995.
Myers et al., Human papillomaviruses, pp II-E6-1-II-E6-7, 1994.
van Ranst et al., J. Gen. Virol. 73: 2653-2660, 1992.
Crook et al., Cell 67: 547-556, 1991.
Dala et al., J. Virol. 70: 683-688, 1996.
Nakagawa et al., Virology 212: 535-542, 1995.
Vousden et al., J. Virol. 63: 2650-2656, 1989.
Bartsch et al., EMBO J. 11: 2283-2291, 1992.
Bosch et al., J. Virology 64: 4743-4754, 1990.
Tummino et al., Proc. Natl. Acad. Sci. USA 93: 969-973, 1996.
Rice et al., J. Medicinal Cham. 39: 3606-3616, 1996.
Rice et al., Science 270: 1194-1197, 1995.
Huibregtse et al., Mol. Cell Biol. 13: 775-784, 1993.
Polyak et al., Nature 389: 300-305, 1997.
Scheffner et al., Proc. Natl. Acad. Sci. USA 91: 8797-8801, 1994.
White et al., Genes Dev. 8: 666-677, 1994.
Tan et al., Cancer Res 55: 4599-4605, 1995.
Beerheide et al., J. Natl. Cancer Inst. 91: 1211-1220, 1999.
Beerheide et al., Bioorganic and Medicinal Chemistry 8: 2549-2560, 2000.
Schifmann, Journal of the National Cancer Institute 87: 1345-1347, 1995.
Edmonds and Vousden, Journal of Virology 63: 2650-2656, 1989.
International Agency for Research on Cancer, IARC Monographs on the evaluation of carcinogenic risks to humans, vol. 64: Human papillomaviruses, 1995, IARC, Lyon, France.
Frederickson et al., J. Neurosci. Meth. 20: 91-103, 1987.
Lehman et al., Carcinogenesis 14: 833-839, 1993.
von Knebel et al., Int. J. Cancer 52: 831-834, 1992.
Derwent Abstract Accession No: 92-303542/37, B05, JP 4-208223, Jul. 27, 1992, Kawaguchi Kagaku Kogyo KK).
Synlett, Aug. 1990, Katritzky, Alan R. et al., "The Synthesis of Bis(N,N-disubstituted amino) Trisulphides".
Derwent Abstract Accession No: 95-340184/44, B05, JP 7-233057 A, Kinki Daigaku GH, Sep. 5, 1995.
Brain Research vol. 44, No.: 2 (1972), Lycke, E. et al., "The Monoamine Metabolism in Virol Encephalitides of the Mouse II, Turnover of Monoamines in Mice Infected with Herpes Simplex Virus".

(Continued)

*Primary Examiner*—Christopher S. F. Low
*Assistant Examiner*—Brian-Ying S. Kwon
(74) *Attorney, Agent, or Firm*—Bacon & Thomas

(57) ABSTRACT

The invention provides agents and compounds (see (I) and (II)) for use in the treatment or prophylaxis of disease conditions caused or exacerbated by mammalian papillomaviruses, such as human papillomaviruses, as well as methods for the treatment or prevention thereof. In said formulae, $R^1$–$R^4$ and n are as defined herein.

24 Claims, 5 Drawing Sheets

OTHER PUBLICATIONS

Derwent Abstract Accession No: 86-282536/43, B03, C02, JP 1207376A, Toyo Soda Mfg. KK, Sep. 13, 1986.

Derwent Abstract Accession No: 88-245781/35 A12, JP 3-178148 A, Nippon Oil Seal Ind, Jul. 22, 1988.

Derwent Abstract Accession No: 91-038784/05, S03, JP 2-304346 A, Nihon Parkerizing, Dec. 18, 1990.

Derwent Abstract Accession No: 91-122584/17, B03, JP 3-063258 A, Kuraray KK, Mar. 19, 1991.

Virology vol. 243, pp. 287-292, 1998, Ott, David E. et al., "Inhibition of Friend Virus Replication by a Compound that Reacts with the Nucleocapsid Zinc Finger: Anti-retroviral Effect Demonstrated in Vivo", abstract: fourth, fifth, tenth and twelfth compounds of Table 1.

Journal of Medicinal Chemistry, vol. 40, No: 13 (1997) pp. 1969-1976, McDonnell, Nazli, B. et al., "Zinc Ejection as a New Rationale for the Use of Cystamine and Related Disulfide-containing Antiviral Agents in the Treatment of AIDS", abstract; figures 1, 2; Table 1; p. 1973 last paragraph to p. 1974 first paragraph.

Techniques in Protein Chemistry VIII (Symp Protein Soc), 10th (1997), Meeting Date 1996, pp. 231-244, Chertova, E. et al., "Reaction of HSV-1 NC p7, Zinc Fingers with Electrophilic Reagents", pp. 231-232, 235-237, 241-242.

Drug Metabolism and Disposition: The Biological Fate of Chemicals, vol. 24, No: 12 (1996), pp. 1395-1400 (Hathout, Yetrib et al.), "Characterisation of Intermediates in the Oxidation of Zinc Fingers in Human Immunodeficiency Virus Type I Nucleocapsid Protein P7", abstract, figure 1, p. 1397, column I, second paragraph, p. 1398, column 2, second paragraph.

Journal of Medicinal Chemistry, vol. 39, No: 19 (1996) pp. 3606-3616 (Rice, William G. et al), "Evaluation of Selected Chemotypes in Coupled Cellular and Molecular Target-Based Screens Identifies Novel HIV-I Zinc Finger Inhibitors", abstract, p. 3608 column 2 last paragraph, Table 10.

Journal of Virology, vol. 70, No: 8 (1990) pp. 4966-4972 (Rein, Alan et al.), "Inactivation of Murine Leukemia Virus by Compounds that React with the Zinc Finger in the Viral Nucleocapsid Protein", abstract, p. 4970 first paragraph.

Carcinogenesis, vol. 9, No: 9 (1988) pp. 1547-1551 (Rotstein, Joel B. et al), "Effect of Exogenous Glutathione on Tumour Progression in the Murine Skin Multistage Carcinogenesis Model", abstract, p. 1547 last paragraph to p. 1548 first paragraph, p. 1549 first paragraph, figure 2.

Chemical Abstracts 102:8009 Rubber Chem Technol (1984), vol. 57 No: 4 pp. 744-754 RN 86796-75-0, 86796-78-3, 86796-79-4.

Chemical Abstracts 111:146042 Chromatographia (1989) vol. 27 No: 3-4 pp. 113-117.

Chemical Abstracts; RN 95255-69-9.

Chemical Abstracts; RN 103-34-4.

SEQUENCE LISTING

```
<160> NUMBER OF SEQ ID NOS: 2

<210> SEQ ID NO 1
<211> LENGTH: 158
<212> TYPE: PRT
<213> ORGANISM: Human papillomavirus type 16

<400> SEQUENCE: 1

Met His Gln Lys Arg Thr Ala Met Phe Gln Asp Pro Gln Glu Arg Pro
 1               5                  10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence:
      Illustrative zinc domain peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(33)
<223> OTHER INFORMATION: Variable amino acid
<220> FEATURE:
```

-continued

```
<221> NAME/KEY: MOD_RES
<222> LOCATION: (35)..(36)
<223> OTHER INFORMATION: Variable amino acid

<400> SEQUENCE: 2

Cys Xaa Xaa Cys Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
                20                  25                  30

Xaa Cys Xaa Xaa Cys
            35
```

METHOD OF TREATING A DISEASE CONDITION CAUSED OR EXACERBATED BY AN HPV

FIELD OF INVENTION

The present invention relates generally to agents useful in the treatment or prophylaxis of viral mediated disease conditions. More particularly, the present invention provides therapeutic agents useful in the treatment of cervical cancer, genital warts or asymptomatic infections caused or otherwise exacerbated by a mammalian papillomavirus (MPV). The present invention is further directed to methods of treatment using said agents as well as methods of identifying same.

BACKGROUND OF THE INVENTION

Viral mediated disease conditions represent some of the most debilitating diseases affecting humans and animals and are responsible for significant mortality and morbidity. This is particularly the case for cancers associated with viral transformation of host cells. One particularly serious form of cancer is cervical cancer. Persistent infection of the transformation zone of the cervix uteri with MPVs such as human papillomavirus (HPV) is seen as a primary cause of cervical cancer. Approximately half a million women die of cervical cancer every year, while a much higher number of patients are exposed to preinvasive disease or genital warts, and one has to conclude that treatment of these virally caused neoplasias is still inadequate in spite of the long-term establishment of surgical techniques.

MPV genomes encode proteins with molecular properties required for cellular transformation in cell culture and in situ. Human papillomavirus-16 (HPV-16) is the most common HPV type in malignant neoplasia and is found in about 60% of all cervical carcinomas, while about twenty other HPV types account for another 30% of these malignancies. Other HPV types that infect genital mucosa or skin, like HPV-6 and HPV-11, are most often associated with benign neoplasia, such as genital warts.

Current treatment for HPV-16 associated lesions is surgery, while limited success is achieved for HPV-6 and HPV-11 lesions with immune modulators like interferon. Prevention of infection by HPV by vaccination and challenge of established HPV infections by immune therapy are under intense investigation, but are presently not established clinical procedures.

A need exists, therefore, for further therapeutic agents useful in the treatment or prophylaxis of disease conditions caused or exacerbated by MPVs and for methods of identifying same.

SUMMARY OF INVENTION

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

One aspect of the present invention provides an agent useful in the treatment or prophylaxis of a disease condition caused or exacerbated by an MPV, said agent comprising a compound capable of reducing, inhibiting or otherwise decreasing the activity of a protein encoded by an MPV gene where said agent facilitates disruption of a chelated metal cation domain present in said protein.

Still yet another aspect of the invention contemplates a composition comprising a compound capable of facilitating the disruption of a chelated metal cation domain of a protein encoded for by an MPV gene, together with a pharmaceutically acceptable carrier, diluent or excipient.

Yet a further aspect of the invention relates to a method of treating or preventing a disease condition caused or exacerbated by an MPV comprising the administration of an effective amount of a compound capable of facilitating the disruption of a chelated metal cation domain of a protein encoded for by an MPV gene to a mammal in need thereof.

Another aspect of the invention provides the use of a compound capable of facilitating the disruption of a chelated metal cation domain of a protein encoded for by an MPV gene in the manufacture of a medicament for the treatment or prophylaxis of a disease condition caused or exacerbated by an MPV.

A further aspect of the invention relates to a composition comprising at least one compound according to Formula I or Formula II as herein described together with a pharmaceutically acceptable carrier, diluent or excipient.

In another aspect, the present invention provides a method of treating or preventing a disease condition caused or exacerbated by an MPV comprising the administration of at least one compound according to Formula I or Formula II as herein described to a mammal in need thereof.

Yet a further aspect of the invention provides a use of at least one compound of Formula I or II as herein described in the manufacture of a medicament for the treatment or prophylaxis of a disease condition exacerbated by an MPV.

Still another aspect of the invention provides an agent for the treatment or prophylaxis of a disease condition caused or exacerbated by a MPV comprising at least one compound of Formula I or II as herein described.

Preferably, the MPV is a human papilloma virus (HPV).

Figure 1:
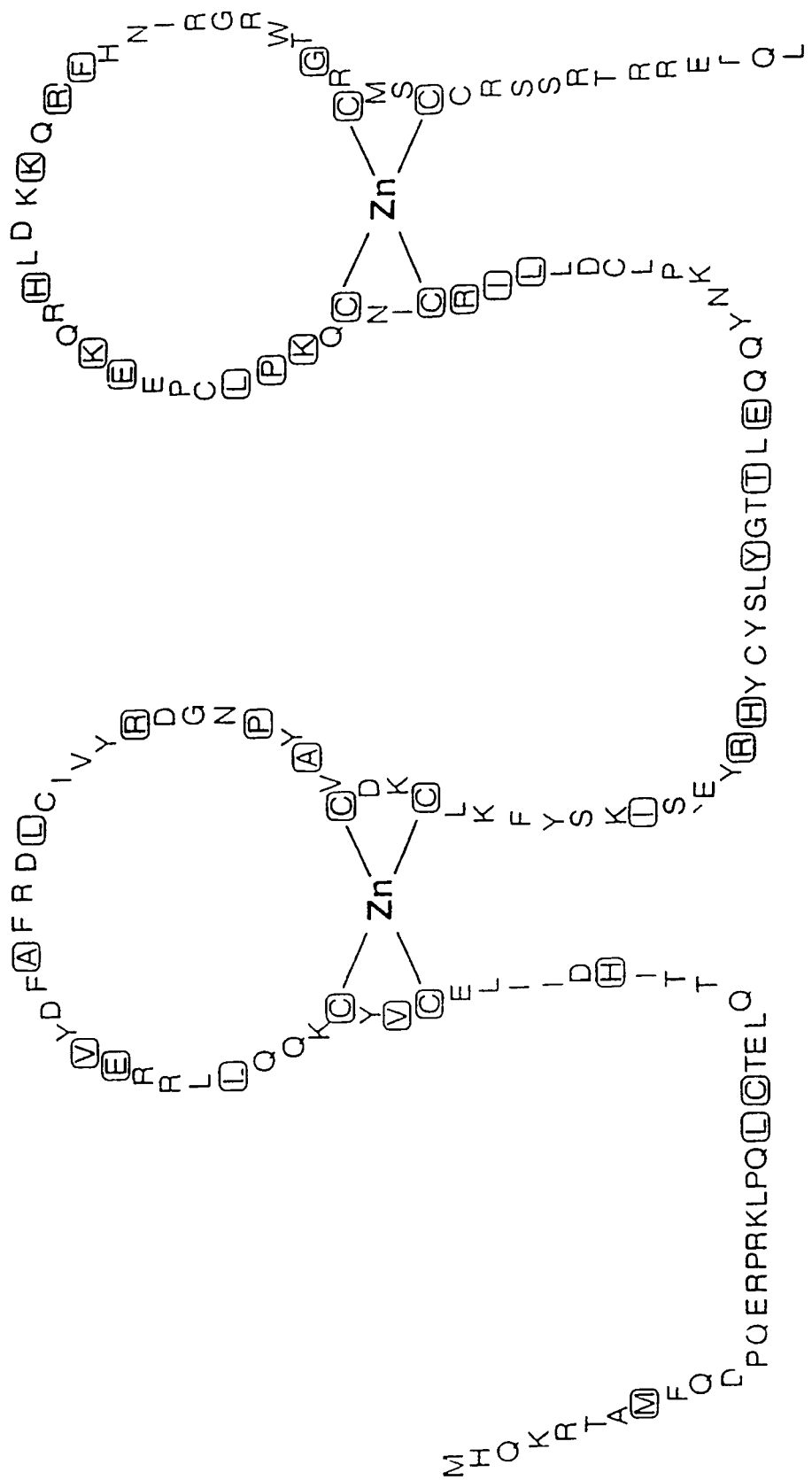
FIG. 1 diagrammatically depicts the E6 protein of SEQ ID NO:1 which consists of 158 amino acids, with two Cys-X2-Cys-X29-Cys-X2-Cys (SEQ ID NO:2) zinc fingers forming the most conspicuous secondary structure. Amino acid residues shown by encircled letters are conserved among HPV-6, HPV-11, HPV-16 and HPV-18. HPV-16 and HPV-18 are the most prevalent papillomaviruses in carcinomas of the cervix precursor lesions.

The following single and three letter abbreviations are used for amino acid residues:

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

DESCRIPTION OF THE PREFERRED EMBODIMENTS

The agents of the present invention are especially useful in the treatment of disease conditions caused by an MPV such as HPVs. HPV infection is implicated in cervical carcinomas, genital warts, common warts, plantar warts and planar warts. Cancerous conditions which are due to HPV infection can be classified according to their state of malignancy, for example:

Malignant carcinoma of the cervix—(CaCx)
Carcinoma of the cervix in situ —CIS (also called CIN III)
Cervical intraepithelial neoplasia —CIN I and CIN II (also called SIL-squamous intraepithelial lesions)
ASCUS—atypical squamous cells of the undetermined significance, as lesions detected by Papanicolaou smears or latent HPV infection detected by DNA hybridization.
Warts can also be classifed according to various types, e.g., genital, common, plantar and planar warts.

Disease conditions which may especially be treated in accordance with the present invention are cervical cancer or precursor lesions of this malignant neoplasia, which are called cervical intraepithelial neoplasia (CIN) or squamous intraepithelial lesions (SIL). The agent may also be useful in the treatment of asymptomatic infections of the cervix in patients identified by DNA diagnosis, or asymptomatic infections that are assumed to remain after surgical treatment of cervical cancer, CIN or SIL, or asymptomatic infections presumed to exist following epidemiological reasoning. The disease conditions to be treated also include genital warts, and common warts and plantar warts. All of these conditions are also caused by a large number of other HPV types, and the agents, compounds and methods of the invention may also be usefully directed against these viruses. All of these lesions presumably derive from asymptomatic infections, that are most often not diagnosed. The present invention may also be usefully targetted against all of these asymptomatic infections.

HPVs frequently associated with cervical carcinoma are HPV-16, HPV-18, HPV-31, HPV- 33, HPV-35 and HPV-45. Those frequently associated with genital warts are HPV-6 and HPV-1; those commonly associated with common warts are HPV-2, HPV-27 and HPV-57; those with plantar warts HPV-1 and those with planar warts are HPV-3 and HPV-4.

Other, types of known HPVs, infection by which may be treated in accordance with the invention, are depicted on Table 1 of page 37 of *Human Papillomarviruses* [Volume 64 (1995) IARC Monographs on the evolution of carcinogenic risks in Humans, The International Agency for Research on Cancer, World Health Organisation, IARC, Lyon, France], which Table is incorporated herein by reference.

All HPVs have circular double stranded DNA genomes with sizes close to 8 kb. The genomes of different HPV types can be aligned, and there are eight genes that are homologous among all genital HPV types. These genes contain many sequence similarities, which suggest similar and conserved (although not necessarily identical) functions. The transforming properties of one HPV-16 originate from three oncoproteins that are the products of the genes E5, E6, and E7. These proteins have pleotropic effects with consequences for transmembrane signalling, regulation of cell cycle, transformation of established cell lines, immortalization of primary cell lines, and chromosomal stability (1,2). The E6 oncoprotein can form a ternary complex with the cell cycle regulator p53 and E6 associated protein, E6AP, with the result of degradation of p53 by the ubiquitination pathway (3,4). In another mechanism, the E6 protein can bind to E6BP (also called ERC-55), a calcium binding protein localized in the endoplasmic reticulum, with possible consequences for intracellular signalling (5). E6 changes cellular morphology, as it interacts with paxillin and thereby disrupts the actin cytoskeleton (6). E6 has also been described to activate (7,8) or, alternatively, repress transcription (9), to stimulate telomerase (10), to immortalize primary cell cultures (1, 2) and to interfere with the differentiation of human keratinocytes (4).

The E6 protein of HPV-16 (FIG. 1) has a size of 158 amino acids. Its most conspicuous sequence motifs are two Cys-X2-Cys-X29-Cys-X2-Cys (SEQ ID NO:2) zinc fingers (11–13). Analysis of Swiss-Prot database indicates that this sequence motif is unique for papillomavirus E6 and E7 proteins (14), and includes numerous specific amino acids residues, highly conserved among all carcinogenic HPVs as well as many animal and human papillomavirus associated with benign lesions. The homology between all papillomavirus E6 genes permits the alignment of their nucleotide sequences, forming a useful database to establish papillomavirus taxonomy (15–17). A similar zinc finger is found in the E7 protein. The extreme conservation of E6 and E7 zinc fingers among viruses with otherwise significant sequence diversity suggests that this zinc-binding motif is required for the structure and the function of HPV E6 and E7 oncoproteins, and it has been shown that mutations affecting the HPV-16 and the bovine papillomavirus type 1 (BPV-1) E6 zinc fingers interfere with cellular transformation as well as with complex formation between E6 and E6AP and E6BP.

The structure and function of the HPV-16 E6 oncoprotein depends on the integrity of the zinc fingers, in which the sulhydryl-groups of four cysteines serving as metal-chelating residues.

The precise role of E6 in the etiology of cervical cancer is difficult to assess directly, but rather has to be inferred mostly from information on E6 function in cell culture or animals systems or molecular studies in vitro. The presently available knowledge suggests functions of E6 (and E7) in situ in three different pathological scenarios. (i) In stratified epithelia, uninfected epithelial cells differentiate without further mitoses after they left the basal and became part of the suprabasal layers. After infection by HPVs, E6 and E7 proteins interfere with this normal repression of mitosis. The consequence is a dedifferentiated and expanded cell population with HPV genomes and the progression from a clinically latent infection into a benign intraepithelial neoplasia. (ii) In these benign lesions, E6 and E7 maintain a high frequency of aberrant mitoses leading to chromosomal aberrations and aneuploidies, raising the chance for generation of increasingly tumorigenic cellular variants (32). (iii) Continuous expression of E6 and E7 may be required for continuous proliferation of malignant tumours and metastases (33, 34, 24). Anti-E6 and anti-E7 drugs should desirably be able to interfere with HPV lesions on all three levels of carcinogenesis. Accordingly, the compounds described herein may be useful in therapeutic or prophylactic applications where these pathological scenarios are implicated.

Accordingly, one aspect of the present invention provides an agent useful in the treatment or prophylaxis of a disease condition caused or exacerbated by an MPV, said agent comprising a compound capable of reducing, inhibiting or otherwise decreasing the activity of a protein encoded by an MPV gene where said agent facilitates disruption of a chelated metal cation domain present in said protein.

As used herein, the term "chelated metal cation domain" refers to the structure of a protein molecule formed by chelation or association of a metal cation with two or more non-adjacent amino-acid residues. The amino acid residues may reside on a single protein molecule to form a "finger" or, alternatively, reside on different protein molecules to form, for example, a dimer. In a preferred embodiment, the metal cation is selected from manganese, iron, cobalt, nickel, copper or zinc. Most preferably, the metal is zinc. In another embodiment, the metal cation is chelated to four amino acid residues. In yet another embodiment of the invention, the metal atom is chelated to at least one cysteine residue, preferably via the sulfhydryl group.

In yet a more preferred embodiment the chelated metal cation domain is a zinc domain in which the sulfhydryl groups of four cysteine residues are chelated to the zinc cation. In still yet a more preferred embodiment, the zinc domain comprises the Cys-X2-Cys-X29-Cys-X2-Cys (SEQ ID NO:2) sequence motif, wherein the zinc atom is chelated to the four Cys residues via the sulfhydryl groups (see FIG. 1).

As used herein, a protein molecule encoded for by an MPV gene refers to a peptide, polypeptide or other amino acid sequence translated from a gene in an MPV genome, or derivative thereof. Preferably, the MPV is an HPV, more preferably HPV-16 or HPV-18. In a preferred embodiment the gene is HPV-16 E6, HPV-16 E7, HPV-18 E6 or HPV-18 E7. Most preferably the gene is HPV-16 E6. Preferably, the protein is the E6 or E7 oncoprotein.

Compounds which may be useful in the treatment of diseases and conditions caused by MPVs include compounds of the general Formula (I)

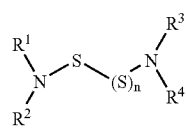

(I)

wherein
n is selected from 1–5
$R^1$–$R^4$ are independently selected from hydrogen, optionally substituted alkyl, optionally substituted alkenyl, optionally substituted alkynyl, optionally substituted aryl, optionally substituted arylalkyl optionally substituted acyl, optionally substituted heterocyclyl, halo alkyl, arylalkyl, carboxy, carboxy ester and carboxamido; or
$R^1$ and $R^2$ together, and/or $R^3$ and $R^4$ together, independently form a group of formula (a):

(a)

wherein:
U is selected from $CH_2$, O, NH or S;
l and n are independently selected from 0 to 6 and m is 0 or 1 when U is $CH_2$ and m is 1 when U is O, NH or S, such that l+m+n is greater than or equal to 2;
and wherein any one or more ($CH_2$) or NH groups may be further optionally substituted;

or a pharmaceutically acceptable derivative thereof.

As used herein the term "alkyl", denotes straight chain, branched or cyclic fully saturated hydrocarbon residues. Unless the number of carbon atoms is specified the term preferably refers to $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein the term "alkenyl" denotes groups formed from straight chain, branched or cyclic hydrocarbon residues containing at least one carbon—carbon double bond including ethylenically mono-, di- or poly-unsaturated alkyl or cycloalkyl groups as previously defined. Unless the number of carbon atoms is specified the term preferably refers to $C_{1-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein the term "alkynyl" denotes groups formed from straight chain, branched or cyclic hydrocarbon residues containing at least one carbon—carbon triple bond including ethynically mono-, di- or poly-unsaturated alkyl or cycloalkyl groups as previously defined. Unless the number of carbon atoms is specified the term preferably refers to $C_{1-20}$ alkynyl. Examples include ethynyl, 1-propynyl, 2-propynyl, and butynyl isomers, and pentynyl isomers.

The term "heterocyclic" or "heterocyclyl" denotes mono- or polycarbocyclic groups wherein at least one carbon atom is replaced by a heteroatom, preferably selected from nitrogen, sulphur and oxygen. Suitable heterocyclic groups include N-containing heterocyclic groups, such as, unsaturated 3 to 6 membered heteromonocyclic groups containing 1 to 4 nitrogen atoms, for example, pyrrolyl, pyrrolinyl, imidazolyl, imidazolinyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidyl, pyrazolidinyl or piperazinyl;

condensed saturated or unsaturated heterocyclic groups containing 1 to 5 nitrogen atoms, such as, indolyl, isoindolyl, indolinyl, isoindolinyl, indolizinyl, isoindolizinyl, benzimidazolyl, quinolyl, isoquinolyl, indazolyl, benzotriazolyl, purinyl, quinazolinyl, quinoxalinyl, phenanthradinyl, phenathrolinyl, phthalazinyl, naphthyridinyl, cinnolinyl, pteridinyl, perimidinyl or tetrazolopyridazinyl;

saturated 3 to 6-membered heteromonocyclic groups containing 1 to 3 oxygen atoms, such as tetrahydrofuranyl, tetrahydropyranyl, tetrahydrodioxinyl, unsaturated 3 to 6-membered hetermonocyclic group containing an oxygen atom, such as, pyranyl, dioxinyl or furyl;

condensed saturated or unsaturated heterocyclic groups containing 1 to 3 oxygen atoms, such as benzofuranyl, chromenyl or xanthenyl;

unsaturated 3 to 6-membered heteromonocyclic group containing 1 to 2 sulphur atoms, such as, thienyl or dithiolyl;

unsaturated 3 to 6-membered heteromonocyclic group containing 1 to 2 oxygen atoms and 1 to 3 nitrogen atoms, such as, oxazolyl, oxazolinyl, isoxazolyl, furazanyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl, thiazolinyl or thiadiazoyl;

saturated 3 to 6-membered heteromonocyclic group containing 1 to 2 sulphur atoms and 1 to 3 nitrogen atoms, such as, thiazolidinyl, thiomorphinyl; and unsaturated condensed heterocyclic group containing 1 to 2 sulphur atoms and 1 to 3 nitrogen The term "acyl" denotes carbamoyl, aliphatic acyl group or acyl group containing an aromatic ring, which is referred to as aromatic acyl, or a heterocyclic ring, which is referred to as heterocyclic acyl, preferably $C_{1-20}$ acyl. Examples of suitable acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The term "optionally substituted" is intended to denote that a group may or may not be further substituted or fused (so as to form a condensed polycyclic group) with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocycloamino, haloheterocyclyl, alkylsulphenyl, arylsulphenyl, carboxy, carboxy ester, carboxamido, carboaryloxy mercapto, alkylthio, benzylthio, acylthio, cyano, nitro, sulfate and phosphate groups. As used herein, the term "optionally substituted" may also refer to the replacement of a —$CH_2$— group by a >C=O (carbonyl) group. Where valency constraints allow, one or more optional substituents may themselves be further optionally substituted.

Suitable optional substituents for NH include alkyl, such as methyl, ethyl, propyl and butyl; aryl, such as optionally substituted phenyl; arylalkyl, for example benzyl; heterocyclyl, such as pyridyl, pyrazinyl, pyrimidinyl; and acyl, such as acetyl, carbamoyl (—C(O)—O-alkyl).

The terms "alkoxy, "alkenoxy and "alkynoxy respectively denote alkyl, alkenyl and alkynyl groups as hereinbefore defined when linked by oxygen.

Where appropriate, any one or more of groups $R^1$–$R^4$ and/or their optional substituents may be further protected by a protecting group. Suitable protecting groups are known to those skilled in the art and are described in *Protective Groups in Organic Synthesis*, T. W. Greene and P. Wutz, John Wiley and Son 2nd Edition (1991) the contents of which are incorporated herein by reference and include for example alkylated and acylated oxy and amino groups and the formation of methylenedioxy groups from two vicinal or ortho-proximated hydroxy substituents.

The term "halogen" denotes fluorine, chlorine, bromine or iodine.

The term "aryl" denotes single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl, each of which may be further optionally substituted.

The term "haloalkyl" refers to an alkyl group, as herein before defined, substituted by one or more halogen atoms, eg, $CH_2F$, $CH_2Cl$, $CH_2Br$, $CF_3$, $CCl_3$ $CBr_3$ $CH_2CH_2Br$ or $CH_2CH_2Cl$.

The term "arylalkyl" is intended to refer to an alkyl group, as herein before defined, substituted by an aryl group, as herein before defined, for example, benzyl, ethylphenyl.

In a preferred embodiment, $R^1$ and $R^2$ together and/or $R^3$ and $R^4$ together form a group of formula (a). Suitably, when $R^1$ and $R^2$ together, or $R^3$ and $R^4$ together, independently form a group of formula (a), U is $CH_2$ and m is 1. More preferably, the group of formula (a) is selected from one of $—(CH_2)_2—$, $—(CH_2)_3—$, $—(CH_2)_4—$, $—(CH_2)_5—$, $—(CH_2)_6—$ or $—(CH_2)_7—$. In yet another embodiment, the alkylenyl chain formed by $—(CH_2)_l—U_m—(CH_2)_n—$ is mono- or di-substituted at one or more $—CH_2—$ groups by an optional substituent, as herein before defined, for example; methyl, ethyl, n-propyl, iso-propyl, hydroxy, halo, methoxy, ethoxy, iso-propoxy, acetoxy, and phenyl.

In another preferred embodiment of formula (a), U is NH, O, or S and m is 1. More preferably, $R^1$ and $R^2$, and/or $R^3$ and $R^4$, together with the nitrogen to which they are attached form a group, selected from:

which may be optionally substituted by one or more groups at one or more carbon atoms, and/or, where U is NH, at the nitrogen atom as hereinbefore described.

In a preferred embodiment of the invention, $R^1$ and $R^2$ and/or $R^3$ and $R^4$ together with the nitrogen to which they are attached, each may independently form an optionally substituted morpholino, thiomorpholino or piperizino group.

Another group of compounds which may be suitable for use in the present invention are those of Formula (II):

(II)

or a pharmaceutically acceptable derivative thereof, wherein $R^1$–$R^4$ are as defined for Formula I. In preferred embodiments of Formula (II), $R^1$ and $R^2$ and/or $R^3$ and $R^4$ together form a group of formula (a) as hereinbefore described.

The compounds for use in the present invention, suitably those of Formula (I) or (II), may be administered in a single dose or a series of doses. While it is possible for the active ingredient to be administered alone, it is preferable to present it as a composition, preferably as a pharmaceutical composition.

Accordingly, yet another aspect of the invention contemplates a composition comprising a compound capable of facilitating the disruption of a chelated metal cation domain of a protein encoded for by an MPV gene, together with a pharmaceutically acceptable carrier, diluent or excipient.

The invention also provides a composition comprising a compound according to Formula (I) or (II) together with a pharmaceutically acceptable excipient, carrier or diluent.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, lozenges, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

Tablets may optionally be provided with an enteric coating, to provide release in parts of the gut other than the stomach.

Compositions suitable for topical administration may be presented as solutions or suspensions, creams, lotions, ointments, powders, plasters or bandages.

Compositions for rectal administration may be presented as a suppository with a suitable base comprising, for example, cocoa butter.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

In yet another aspect of the invention, there is provided a method of treating or preventing a disease condition caused or exacerbated by an MPV comprising the administration of an effective amount of a compound capable of facilitating the disruption of a chelated metal cation domain of a protein encoded by an MPV gene to a mammal in need thereof.

The invention also relates to a method of treating or preventing a disease which is caused or exacerbated by an MPV comprising the administration of a compound according to Formula (I) or (II) to a mammal in need thereof.

The present invention also relates to the use of a compound capable of facilitating the discreption of a chelated metal cation domain of a protein encoded by an MPV gene in the manufacture of a medicament for the treatment or prophylaxis of a disease condition caused or exacerbated by an MPV.

As used herein, the term "effective amount" relates to an amount of compound which, when administered according to a desired dosing regimen, provides the desired therapeutic or prophylactic activity. The desired dosing regimen may depend on the weight, age and condition of the patient. It is within the skills and knowledge of the attending physician to determine suitable dosing regimens based thereon. Dosing may occur at intervals of minutes, hours, days, weeks, months or years or continuously over any of these periods. Suitable dosages may lie within the range of about 0.1 ng per kg of body weight to 1 g per kg of body weight per dosage. The dosage is preferably in the range of 1 µg to 1 g per kg of body weight per dosage such as 1 mg to 1 g per kg of body weight per dosage. Suitably, the dosage may be in the range of 1 µg to 500 mg per kg of body weight per dosage, for example in the range of 1 µg to 250 mg per kg of body weight per dosage, or 1 to 100 mg per kg of body weight per dosage, such as 1 µg to 50 mg.

Optionally, the compounds referred to herein may also be administered in the form of a pharmaceutically acceptable derivative. The term "pharmaceutically acceptable derivative" refers to any pharmaceutically acceptable salt, ester, solvate, hydrate or any other compound which, upon administration to the recipient is capable of providing (directly or indirectly) a compound as described herein. Suitable pharmaceutically acceptable salts include salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

The search for anti-viral drugs is hampered when it requires assays that monitor the complete life cycle of a virus in context of the biology of the infected cell or animal. This is primarily because these in vivo assays are time consuming and expensive, and chemical compounds that alter the biology of the infected cells may lead to misinterpretations. In contrast, pure viral proteins expressed from cloned genes allow the development of low-cost and efficient assays specifically designed to measure the effects on the chemistry, structure and function of these proteins. These strategies have been successfully employed recently to identify drugs against several viral diseases, most notably against HIV-1. Similar efforts directed against papillomaviruses are in their infancy, even though these viruses affect several million patients a year worldwide.

Suitable compounds of the invention, such as compounds of Formula (I) and Formula (II) are those which facilitate the disruption of a chelated metal cation domain in a protein encoded for by an MPV gene. Thus, in order to provide an initial evaluation of the efficacy of the compounds useful in the treatment of diseases or conditions caused by MPVs, the ability of these compounds to disrupt the integrity of a chelated metal cation domain, thereby releasing the metal cation, offers a useful assay therefor.

This can be achieved by contacting a protein molecule, encoded by an MPV gene, containing a chelated metal cation domain, with an effective amount of said compound for a time and under conditions sufficient to facilitate disruption of the chelated metal cation domain and directly or indirectly determining the amount of chelated metal cation released wherein the amount of chelated metal cation released is indicative of the disruption of the chelated metal cation domain.

Where the chelated metal is zinc, zinc release can be measured as an increase in the fluorescence of the zinc-selective fluorophore TSQ (N-(6-methoxy-8-quinolyl)-p-toluenesulfonamide) (18) in the presence of the protein and the active compound (TSQ assay).

In such an assay, the increase in fluorescence measured can be described as a percentage of the increase in fluorescence observed for a positive control compound which provides 100% zinc release. A suitable positive control compound is $H_2O_2$. Preferred compounds which may be useful in the present invention are those which release at least 30% of the chelated zinc as measured by the TSQ assay. Particularly preferred compounds for use in the present invention are those which release at least 40% of the chelated zinc, more preferably at least 50%.

Another method of identifying compounds useful in the treatment of a disease condition caused or exacerbated by an MPV comprises contacting a protein molecule, containing a chelated metal cation domain encoded by an MPV gene, with an effective amount of said compound for a time and under conditions sufficient to facilitate disruption of the chelated metal cation domain and directly or indirectly determining the absence or otherwise of binding of said protein to a ligand, wherein the absence of binding is indicative of disruption of the chelated metal cation domain.

Mutation analysis of the cysteines involved in coordinating zinc has demonstrated that zinc binding is a requirement for E6 interaction with E6AP and E6BP, two coactivators of E6 mediated cellular transformation (5, 19–22). Thus, another useful assay for determining suitable compounds which may be used in the present invention measures the ability of the compound to inhibit the binding of the E6 protein to E6AP, E6BP, paxilin or similar or homologue motifs. Thus, suitable compounds which may be used in the present invention are those which are capable of reducing, inhibiting or otherwise decreasing the binding interaction between the E6 protein and E6AP or E6BP. The efficacy of compounds can be evaluated in BIACORE and GST pull-down experiments (binding assay). Preferred compounds are those which inhibit or decrease binding by at least 50%.

Zinc finger proteins are required for maintenance of cell viability. Preferably, the compounds for use in the present invention are specific in their ability to affect the viability of MPV containing cells, with little or no cytotoxic effects on the cellular functioning of healthy non-MPV containing cells. The viability of MPV-infected cells (and non infected cells) in the presence of compounds of Formulae (I) or (II) can be measured by incubating with the tetrazolium salt WST1 (Roche Molecular Biochemicals, Manneheim Germany) and measuring the absorption readings thereof (WST1 assay).

Preferred compounds for use in the present invention produce values of at least 30% zinc release in the TSQ assay and/or inhibit or reduce binding of the E6 protein to E6AP or E6BP and/or exhibit selective cytotoxicity towards MPV-infected cells.

Especially preferred compounds for use in the present invention are those which release at least 30% of chelated zinc from a protein having a chelated zinc domain as measured by the TSQ assay, and inhibit binding of the E6 protein to E6AP or E6BP as measured by the herein described BIACORE assay and selectively inhibit cell growth of MPV-infected cells whilst having little or no cytotoxic effect on non-MPV-infected cells (for example, as determined by the WST1 assay as herein described).

Other preferred compounds inhibit or reduce binding of the E6 protein to E6AP or E6BP by at least 50% and are specifically toxic to MPV-infected cells.

Yet other preferred compounds release at least 50% of chelated zinc and inhibit E6 binding to E6AP or E6BP by at least 50%.

Suitable examples, although by no means to be considered as limiting, are illustrated below, where n=1 to 5:

GROUP 1 TSQ>50% AND BIACORE + AND WST1-SPECIFICITY +

C16

C48

C55

C63

GROUP 2 TSQ>40% AND BIACORE + AND WST1-SPECIFICITY +

C37

C38

C39

GROUP 3 TSQ>30% AND BIACORE + AND WST1-SPECIFICITY +

C41

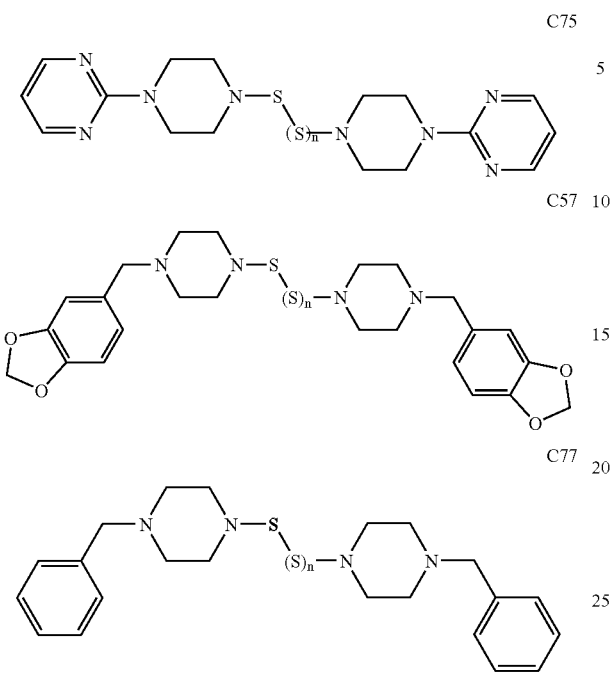
GROUP4 TSQ<30% AND BIACORE + AND WST1-SPECIFICITY +
GROUP 5 TSQ. 50% AND BIACORE +
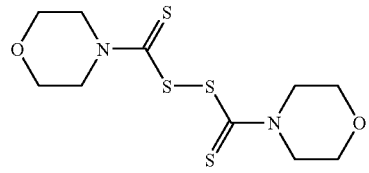
GROUP 6 TSQ> 50% AND BIACORE OR WST1-SPECIFICITY +
The invention will now be described with reference to the following non-limiting examples.

Modes for Carrying Out the Invention

General

Compounds C32 and C35 are available from Aldrich Rare Chemicals (cat # S5, 169-2) and Acros Organic (cat # 22758.60). Compound C16 is available from Tee Hai Chemicals (Singapore).

Role of GSH in Drug-Screens

GSH is, at concentrations of 1–10 mM in most cell types, the most abundant non-protein intracellular thiol, and it is involved in biochemical reactions that can inactivate pharmaceutical compounds. In the original TSQ assays, GSH was present at 5–10 mM. Under these conditions, only a few of the compounds, including C16, were capable of releasing zinc. Increased concentrations of C16 were also required in the GST-pulldown assay, possibly to overcome the endogenous levels of GSH in the reticulolysate extracts. Similarly, in cell viability assays, C16 was only effective at concentrations of 50 μM, exceeding the amount used in TSQ assays five fold. To overcome the inactivating function of GSH, higher amounts of C16 were needed in vivo than in vitro. The TSQ assay is much easier when it comes to high-throughput capabilities to identify lead compounds, while in vivo assays and in vitro assays in the presence of GSH, are useful to select compounds that reach intracellular E6 in sufficiently high concentrations and in chemically unaltered form.

Expression of E6. E6AP as GST-fusion Proteins

E6, E6AP and E6BP-Glutathione S-transferase (GST) fusion proteins were prepared by using pGEX system Amersham (Pharmacia Biotech AB, Uppsala Sweden). The full length HPV16 E6 gene was amplified via polymerase chain reaction and cloned in the vector pGeX4T2 as a Not1-Sal1 insert. A clone encoding the C-terminal 210 amino acids of E6BP/ERC55 in pGEX3X was a kind gift of E. J. Androphy (5). E6AP (amino acids 213WO 865), cloned in pGEX2T was a kind gift of P. M. Howley (28). These vectors were grown in the $E.\ coli$ strain AB1899, induced for fusion protein expression for 4 hrs with 0.2 mM IPTG, harvested and lysed in GST-buffer (Phosphate buffered saline (PBS), 50 mM Tris pH 8.0, 0.1% Triton) with 5 mM dithiothreitol (DTT), 0.5 mM phenylmethylsulfonyl fluoride (PMSF)) and 1 mg/ml lysozyme, followed by sonication. After ultracentrifugation, supernatants of bacterial lysates were incubated at 4° C. on a column of gluthathione-sepharose beads (Pharmacia). Unbound, non GST-fusion proteins were eliminated by several washes with GST-buffer. For direct use of GST-fusion proteins bound on glutathione-sepharose beads in the zinc-release assay, the glutathione-sepharose beads were resuspended in PBS, Tris pH 8.2. GST-fusion proteins for BIACORE analysis were eluted with elution-buffer (10 mM GSH, 50 mM Tris, PBS, pH 8.2).

EXAMPLE 1

General Synthesis of Compounds of Formula (I) and (II)

Compounds of Formula (I) can be prepared by reacting appropriately substituted amines according to the general procedure below.

Alkylation of primary amine ($R^1NH_2$, 0.1 mmol) with alkyl halide ($R^2X$, 0.1 mmol) in acetonitrile (0.5 ml) and diethylamine (0.15 mmol) at 80° C. for 30 min gave the secondary amine ($R^1R^2NH$) after purification on silica gel column.

A solution of the secondary amine (0.5 mmol) in petroleum-ether (10 ml) was pre-cooled to −78° C. before disulfur dichloride (0.125 mmol) was added. The solution was vigorously stirred for 15 minutes at −78° C. and another 30 min at room temperature. Water (20 ml) was added and the desired compound was extracted into the organic phase using diethyl ether (3×10 ml). The combined organic layers were dried over magnesium sulfate, filtered and concentrated in vacuo. The desired compound was purified on preparative TLC plate. Mixtures of amines may be used to prepare unsymmetrical compounds of Formula (I).

Besides the desired disulfide compound, trisulfide, tetrasulfide or pentasulfide compounds may also be obtained. A dilute reaction solution (20 ml) generally results in higher yield of the disulfide compound.

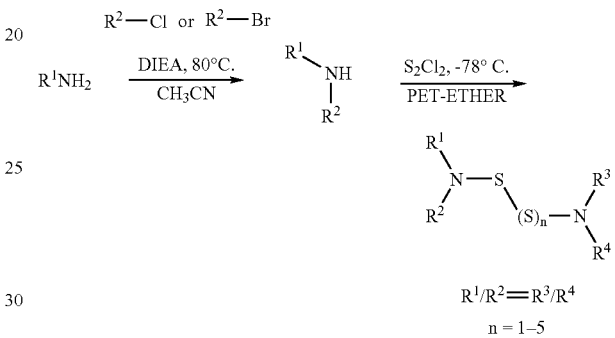

SCHEME 1

Compounds of Formula (II) may be prepared by treatment of a secondary amine (or mixtures thereof) with carbon disulfide in the presence of sodium hydroxide followed by oxidation of the resulting sodium dithiocarbamate with sodium hypochlorite.

Spectroscopic data for a selected number of compounds from Groups 1–6 are presented below.

Group 1

C48 ($C_{10}H_{20}N_2S_2$);
CAS: 10220-20-9
$^1$H NMR (400 MHz, CDCl$_3$) δ: 1.36–1.43 (m, 4H), 1.63–1.70 (m, 8H), 2.77–2.79 (m, 8H).
$^{13}$C NMR (100 MHz, CDCl$_3$) δ: 22.8, 27.0, 57.4.
MS found 233 (M+1)$^+$ C55 ($C_{18}H_{24}N_6S_2$):
$^1$H NMR (400 MHz, CDCl$_3$) δ: 2.92–96 (m, 8H), 3.60–3.61 (m, 8H), 6.63–6.66 (m, 4H), 7.47–7.51 (m, 2H), 8.18–8.19 (m, 2H),
$^{13}$C NMR (100 MHz, CDCl$_3$) δ: 45.8, 55.4, 107.1, 113.6, 137.5, 147.9, 159.0.
MS found 389 (M+1)$^+$.

C63 ($C_6H_{12}N_2S_{n+1}$):
$^1$H NMR (400 MHz, CDCl$_3$) δ: 2.09–2.28 (m, 4H), 3.79–3.83 (m, 8H)
$^{13}$C NMR (100 MHz, CDCL$^3$) δ: 17.6, 56.9, 57.5.
MS found for trisulfide 209 (M+1)$^+$ Group 2

C37 ($C_2H_{24}N_2O_2S_2$):
C37 is a mixture of diastereoisomers.
$^1$H and $^{13}$C NMR were the same as reported in SYNLETT p473, August 1990.
MS found 293 (M+1)$^+$ C38 ($C_8H_{16}N_2S_4$):
$^1$H NMR (400 MHz, $CDCl_3$) δ: 2.71–2.74 (m, 8H), 3.09–3.11 (m, 8H).
$^{13}$C NMR (100 MHz, $CDCl_3$) δ: 28.8, 58.2.
MS found 269 (M+1)$^+$ C39 ($C_{10}H_{22}N_4S_2$):
$^1$H NMR (400 MHz, $CDCl_3$) δ: 2.25 (s, 6H), 2.45 (broad s, 8H), 2.82–2.84 (m, 8H),
$^{13}$C NMR (100 MHz, $CDCl_3$) δ: 45.78, 45.82, 55.57.
MS found 263 (M+1)$^+$.

Group 3

C41 ($C_{14}H_{26}N_4O_4S_2$):
$^1$H NMR (400 MHz, $CDCl_3$) δ: 1.27 (t, J=7.1 Hz, 6H), 2.78 (broad s, 8H), 3.53 (broad s, 8H), 4.14 (q, J=7.1 Hz, 4H).
$^{13}$C NMR (100 MHz, $CDCl_3$) δ: 14.6, 44.1, 55.5, 61.6, 155.3.
MS found 379 (M+1)$^+$ C57 ($C_{24}H_{30}N_4O_4S_{n+1}$):
A mixture of 2 compounds.
$^1$H NMR (400 MHz, $CDCl_3$) δ: 2.50 (broad s, 8H), 3.02–3.09 (m, 8H), 3.36–3.41 (m, 4H), 5.92–5.93 (m, 4H), 6.72–6.75 (m, 4H), 6.84–6.85 (m, 2H).
$^{13}$C NMR (100 MHz, $CDCl_3$) δ:53.1, 56.1, 56.3, 62.4, 100.90, 107.8, 107.9, 109.3, 109.4, 122.1, 122.2, 131.7, 131.8, 146.6, 146.7, 147.7.
MS found pentasulfide 599 (M+1)$^+$ and hexasulfide 631 (M+1)$^+$.

C75 ($C_{16}H_{22}N_8S_{n+1}$)
$^1$H NMR (400 MHz, $CDCl_3$) δ: 3.08–3.10 (m, 8H), 3.90 (broad s, 8H) 6.50–6.54 (m, 2H), 8.31–8.33 (m, 4H).
$^{13}$C NMR (100 MHz, $CDCl_3$) δ: 43.8, 55.1, 110.1, 157.7, 161.4.
MS found for trisulfide 423 (M+1)$^+$ C77 ($C_{22}H_{30}N_4S_{n+1}$)
$^1$H NMR (400 MHz, $CDCl_3$) δ: 2.53 (broad s, 8H), 3.06–3.11 (m, 8H), 3.47 (broad s, 4H), 7.26–7.36 (10H).
$^{13}$C NMR (100 MHz, $CDCl_3$) δ: 53.2, 56.1, 62.7, 127.2, 128.3, 129.1, 137.8.
Multiple S observed.

Group 4

C65 ($C_{24}H_{30}N_4O_2S_2$):
$^1$H NMR (400 MHz, $CDCl_3$) δ: 2.54 (s, 6H), 3.16 (broad s, 8H), 3.42 (broad s, 8H), 6.85–6.89 (m, 4H), 7.87–7.90 (m, 4H).
$^{13}$C NMR (100 MHz, $CDCl_3$) δ: 26.1, 47.9, 55.6, 113.9, 130.4, 153.6, 196.7.

C70 ($C_{22}H_{30}N_4O_2S_{(n+1)}$)
CAS: 15575-30-1
$^1$H NMR (400 MHz, $CDCl_3$) δ: 3.15 (broad s, 8H), 3.28 (broad s, 8H), 3.89 (s, 3H), 3.90 (s, 3H), 6.86–6.90 (m, 2H), 6.93–6.95 (m, 4H), 7.03–7.06 (m, 2H).
$^{13}$C NMR (100 MHz, $CDCl_3$) δ: 50.9, 55.4, 55.5, 55.9, 56.2, 111.2, 118.3, 120.9, 123.2, 140.7, 152.2.
Multiple S observed.

Group 5

C42 ($C_8H_{16}N_2S_2$):
$^1$H NMR (400 MHz, $CDCl_3$) δ: 1.83–1.89 (m, 8H), 2.88–2.91 (m, 8H)
$^{13}$C NMR (100 MHz, $CDCl_3$) δ: 24.9, 55.5.
MS found 205 (M+1)$^+$ C49 ($C_8H_{20}N_2S_2$):
CAS: 15575-30-1
$^1$H NMR (400 MHz, $CDCl_3$) δ: 1.20–1.29 (m, 12H), 2.94–3.07 (m, 8H).
$^{13}$C NMR (100 MHz, $CDCl_3$) δ: 13.2, 51.7, 51.9, 52.0, 52.1.
MS found 208 M$^+$.

Group 6

C71 ($C_{22}H_{30}N_4O_2S_2$):
$^1$H NMR (400 MHz, $CDCl_3$) δ: 3.03 (broad s, 8H), 3.14 (broad s, 8H), 3.77 (s, 6H), 6.83–6.91 (m, 8H).
$^{13}$C NMR (100 MHz, $CDCl_3$) δ: 51.6, 55.5, 55.9, 114.4, 118.6, 145.2, 154.1.
MS found 447 (M+1)$^+$.

C82 ($C_{1020}N_2O_2S_2$):
$^1$H NMR (400 MHz, $CDCl_3$) δ: 1.19 (s, 12H), 3.70 (s, 4H), 4.68 (s, 4H).
$^{13}$C NMR (100 MHz, $CDCl_3$) δ: 24.26, 24.28, 62.00, 79.04, 85.43
MS found 265 (M+1)$^+$.

EXAMPLE 2

Zinc Release (TSQ Assay)

In earlier studies, reduced glutathione (GSH) was required to elute recombinant glutathione sulfhydryl transferase E6 (recombinant (GST-E6)) protein during the purification process. However, the reducing activity of the GSH sulfhydryl groups protected GST-E6 protein from the chemical attack by agents, such as the disulphide based organic compounds of Formula (I) and (II). This problem was overcome by using GST-E6 protein in the absence of free GSH but still bound to glutathione-sepharose beads. Individual assays were done in the presence of 9 μg GST-E6 protein, corresponding to a concentration of 1 μM GST-E6 protein and 2 μM bound zinc, assuming the presence of two Zn ions per protein.

Release of zinc from HPV-16-E6 was monitored by the change in fluorescence of the zinc-selective fluorophore TSQ (N-6-methoxy-8-quinolyl)-p-toluenesulfonamide), (Molecular Probes, Eugene, Oreg.) by modification of published procedures (25, 26, 27). In a total reaction volume of 200 μl, 9 μg (1 μM) recombinant GST-E6 protein (corresponding to a concentration of 1 μM), bound to glutathione-sepharose beads, were incubated with 10 μM of each compound or 0.6% (170 mM) $H_2O_2$ in TSQ-assay buffer (10 mM sodium phosphate buffer pH7.0, 10% glycerol) for 2 hours at room temperature (200 μl total volume in 96-well plates). Immediately after addition of 100 μM TSQ, the increase in fluorescence was measured on a SLT Fluostar (355 nm excitation filter and 460 nm emission filter, Tecan, Salzburg).

Table 1 shows the values of TSQ fluorescence obtained.

TABLE 1

| Compound | TSQ % |
|---|---|
| DMSO | 6.1 |
| C16 | 63.2 |
| C27 | 103 |
| C32 | 80.9 |
| C35 | 106 |
| C37 | 40.3 |
| C38 | 41.8 |

TABLE 1-continued

| Compound | TSQ % |
|---|---|
| C39 | 45 |
| C41 | 36.8 |
| C42 | 50.5 |
| C48 | 54.3 |
| C49 | 57 |
| C55 | 50.6 |
| C57 | 31.1 |
| C63 | 54.8 |
| C65 | 23.7 |
| C69 | 0 |
| C70 | 12.4 |
| C71 | 0 |
| C75 | 37 |
| C77 | 33.8 |
| C82 | 28.4 |
| C83 | 22 |
| R24 | 71.0 |
| R25 | 30.9 |
| R26 | 54.9 |

Values given are % values of Zinc release. The relative fluorescence units (RFU) were normalized to the amount of zinc released by $H_2O_2$ (regarded as 100%). The concentration of compound used was 10 μM for C27–C35, 13 μM for C37–C83, $H_2O_2$ was used at 0.3% for C27–C35 and 0.2% for C37–C83.

Note: C69 was strongly coloured (yellow/golden) at a concentration of 1 mM, all other compounds were without colour. Potentially this coloured compound interferes in TSQ-Zn fluorescence.

Values for DMSO and C16 are the average from 5 independent experiments.

EXAMPLE 3

Binding Assays (BIACORE Assay)

BIACORE allows real time analysis of bimolecular interactions without the need for isotopic or enzymatic labelling. BIACORE technology is based on the optical surface plasmon resonance (SPR), a technique that allows for detecting small changes in the refractive index on the surface of a thin gold film coated with a dextran matrix. Typically, one of the binding partners (termed the ligand) is covalently linked to the dextran matrix, while the other partner (termed the analyte) is introduced in a flow passing over the surface. The change in refractive index resulting from the interaction of the molecules is expressed in resonance units (RU): a SPR response of 1000 RU corresponds to a change of the surface concentration of the analyte of 1 ng protein/$mm^2$. GST-E6AP and GST-E6BP were used as ligands and GSTE6 was used as the analyte. Controls gave the expected outcome, namely the oxidation of sulfhydryl groups by $H_2O_2$ of chelating of zinc ions by EDTA completely eliminated complex formation. Further controls included using the dextran matrix alone or GST as the ligand. GST-E6 did not bind significantly to the dextran matrix or to GST (background values 100 and 200 RU), respectively.

Binding of GST-E6 to GST-E6BP, GST-E6AP and GST was monitored by surface plasmon resonance (SPR) on a BIACORE 2000 machine (Biacore AB, Uppsala, Sweden). Purified ligand (GST, GST-E6AP and GST-E6BP) was covalently amine coupled to a CM-5 sensor chip by activation, binding and deactivation reactions suggested by Biacore AB. Typically 6000–10000 RU of GST, E6BP and E6AP were immobilized on three difference flowcells. Aliquots of purified HPV-16 GST-E6 (7 μM in 10 mM GSH, 50 mM Tris/PBS buffer, pH 8.2) were incubated with either 400 μM compound, or 5 mM EDTA, or 0.6% (170 mM) $H_2O_2$ for 2 hrs at room temperature. Then 10 μl of sample was injected at 1 μl/min over the three immobilized ligands using the sequential flow mode. The interactions between GST-E6 and ligands were monitored by the change of resonance signal in arbitrary units (RU). In between each sample, the surfaces were regenerated with a short 1 minute pulse of 50 mM NaOH that resulted in complete dissociation of all non-covalently bound analyte, leaving the immobilized GST-E6BP and GST-E6AP at approximately full activity. After 20 cycles of binding and regeneration, the amount of E6 binding capacity decreased approximately 18%19% and therefore reduced the maximal amount of E6 binding. Typically complex formation without compound treatment led to signals of 1540–1900RU and 1150–1400 for GST-E6 with GST-E6BP and GST-E6AP, respectively. Absence of a resonance signal, or a reduced signal was scored as an active compound.

The results for the BIACORE binding assay are shown below in Table 2.

TABLE 2

| Compound | BIACORE (E6BP/E6AP) |
|---|---|
| DMSO | − |
| C16 | + |
| C27 | + |
| C32 | + |
| C35 | − |
| C37 | + |
| C38 | + |
| C39 | + |
| C41 | + |
| C42 | + |
| C48 | + |
| C49 | + |
| C55 | + |
| C57 | + |
| C63 | + |
| C65 | + |
| C69 | + |
| C70 | + |
| C71 | − |
| C75 | + |
| C77 | + |
| C82 | + |
| C83 | + |
| R24 | + |
| R25 | + |
| R26 | + |

"+" = compound interferes in binding of E6 with E6AP and E6BP, binding is less than 50% of the corresponding E6-DMSO value.

EXAMPLE 4

Binding of GST Fusion Proteins to in vitro Translated E6 Protein (GST-Pulldown Experiment)

In the BIACORE results, C16 was found to have inhibitory activity for E6 binding to both E6BP and E6AP. On this basis, it was examined whether C16 could also interfere with E6-E6BAP interaction in the GST-pulldown assay. Also, different concentrations of C16 were examined to determine the minimal concentration for inhibitory activity.

The open reading frame of HPV-16 E6, cloned into the Hind III and PstI site of the pSP64 plasmid (33), was in vitro translated with $^{35}S$-cysteine by using the TNT-SP6 Coupled Reticulocyte Lysate System as recommend by the manufacturer (Promega). All washing and binding reactions were performed with the E6BP-binding buffer described (5) but without DTT (100 mM NaCl, 100 mM Tris-HCl pH8.0, 1% NP40, 0.1% nonfat dry milk and 1 mM PMSF. 40 µl of in vitro translated E6 plus 360 µl of E6BP-binding buffer were incubated for 2 hrs at room temperature with test compounds at difference concentrations from 0–1 mM (dissolved in DMSO at 1%), 5 mM EDTA, and $H_2O_2$ at 0.3% (85 mM). The sample was then passed over columns captaining glutathione-sepharose beads with bound GST, GST-E6, GST-E6BP or GST-E6AP proteins. The beads were heated to 95° C. in 50 µl Laemmli sample buffer (BIO-RAD) with 2.5% 2-mercaptoethanol, subjected to electrophoresis on a 15% polyacrylamide gel, fixed, stained, and autoradiographed. Interference with complex formation identified reactive compounds. Desitometric quantification was performed with a BIO-RAD/GS700 imaging desitometer.

Figure 2:
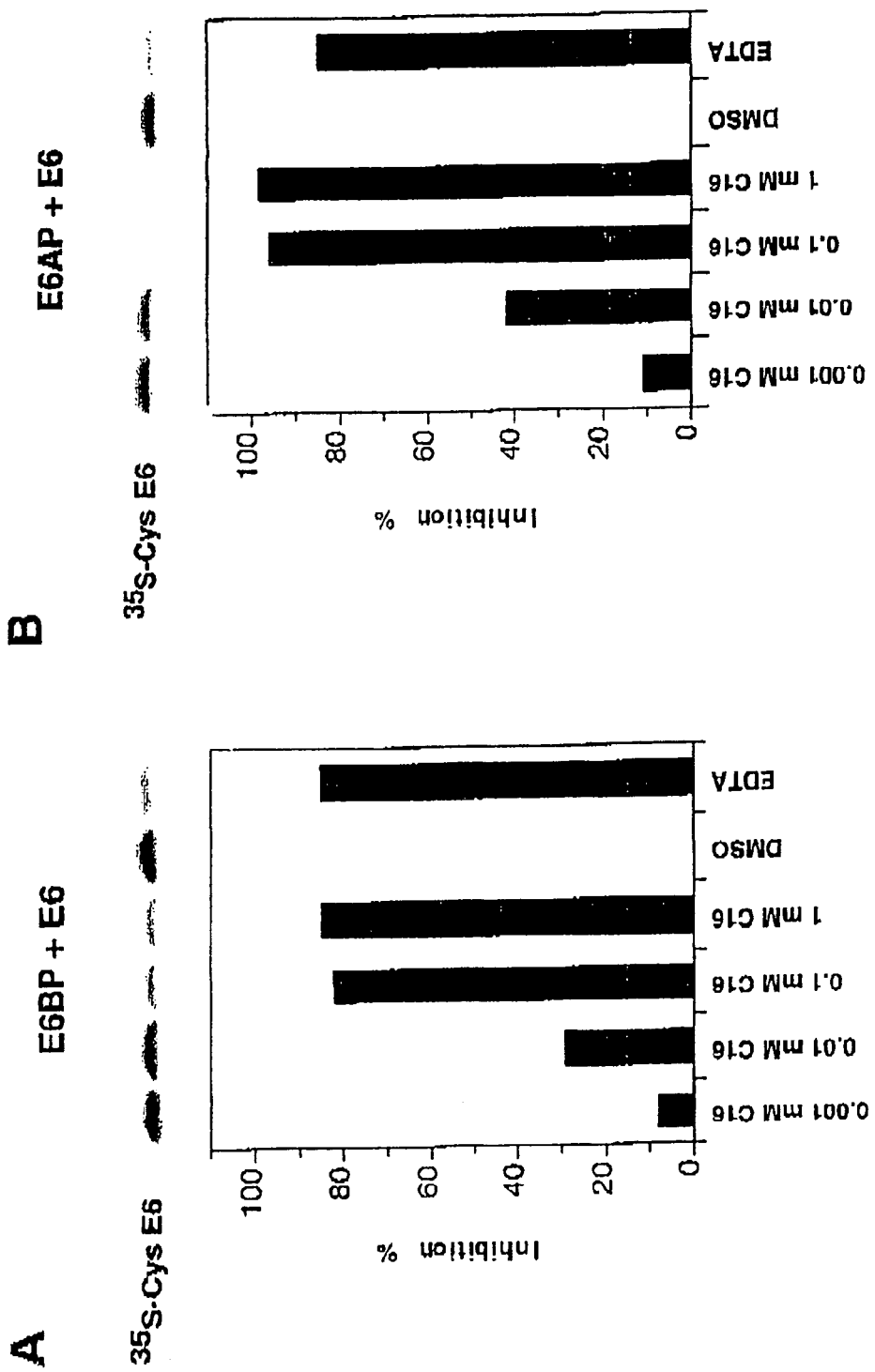
FIG. 2 graphically depicts the effective concentration for C16 under the experimental IVT-assay conditions for E6BP and E6AP. $^{35}$S-Cys E6 was incubated with the indicated concentrations of C16 and assayed for complex formation with E6BP or E6AP. GST reflects the background binding of IVT E6 protein on GST-beads.

As shown in FIG. 2, C16 inhibits E6 binding to both cellular proteins. Of the concentrations examined, concentrations from 10 µM to 100 µM provide greatest inhibitory activity.

EXAMPLE 5

Determination of Cell Viability (WST1 Assay)

All cell lines were obtained from the American Type Culture Collection (Manassas, Va.) unless otherwise noted. SiHa (human cervical epithelial tumor line, HPV16-positive), CaSki (human cervical epithelial tumor line, HPV16-positive), HaCat (immortalized human skin epithelial cell line, HPV-negative), HeLa (human cervical epithelial tumor line, HPV18-positive), 444 (hybrid of HeLa and fibroblast, HPV18-positive) obtained from Eric Stanbridge (University of California, Irvine), MCF7 (human mammary epithelial tumor cell line, HPV-negative), HT3 (human cervical epithelial tumor cell line, HPV-negative) was obtained from the German Cancer Research Institute/DKFZ-Heidelberg, and HepG2, (human liver epithelial tumor cell line, HPV-negative), were grown in Dulbecco's modified Eagle medium (DMEM) supplemented with 10% fetal calf serum, 100 U penicillin and 1000 U streptomycin. Cells were allowed to attach to the surface of microwell dishes overnight and subsequently, incubated with medium containing the zinc ejecting compounds at the concentrations (10–100 µM). Viability of the cells was scored by measuring the absorption of the tetrazolium salt WST1 (Roche Molecular Biochemicals, Mannheim, Germany) in an Elisa-plate reader (Tecan, Salzburg, Austria) at a wavelength of 450 nm and a reference wavelength of 630 nm.

Figure 3:
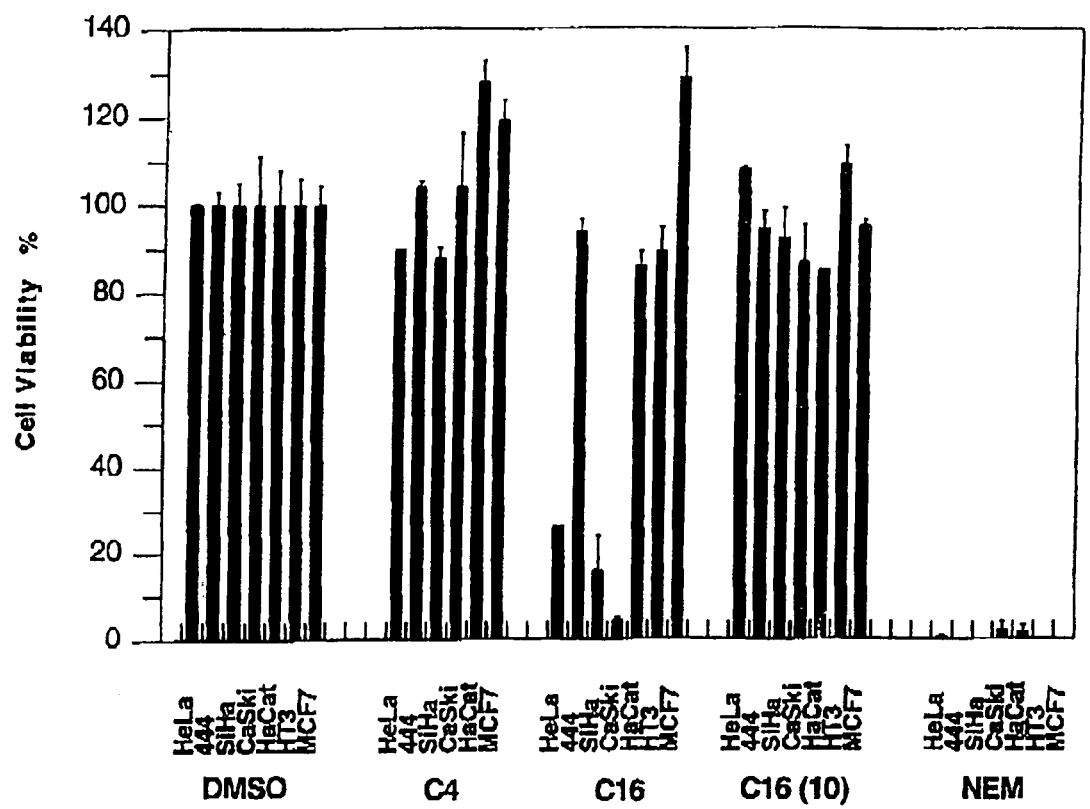
FIG. 3 graphically depicts viability assays of HPV-infected cell lines incubated with C16 and azodicarbonamide (C4). All values were normalized to the values obtained in the presence of DMSO only.

A total of 10 000 cells per well were plated on 24 well plates, after attachment overnight, they were treated 3 times in 3 days with C16 at 10 µM and 50 µM. The activity of C16 was also compared with that of C4 (azodicarbonamide) which causes ejection of zinc from HIV-1 NCp7 and is currently used in clinical trials for the treatment of AIDS. FIG. 3 documents that C4 did not cause growth inhibition in any of these six cell lines while C16 at 50 µM demonstrated substantial and specific inhibition of cell viability in HPV-negative cell lines as cervical epithelial tumour cells (SiHa, Caski, HeLa). C16 had little or no effect on HPV-negative cells as cervical epithelial tumour cells (HT3), mammary epithelial cancer cells (MCF7) and the immortalized skin epithelial cells (HaCat) and on the nontumorigenic (23, 24) HeLa-fibroblast hybrid cell line 444.

Figure 4:
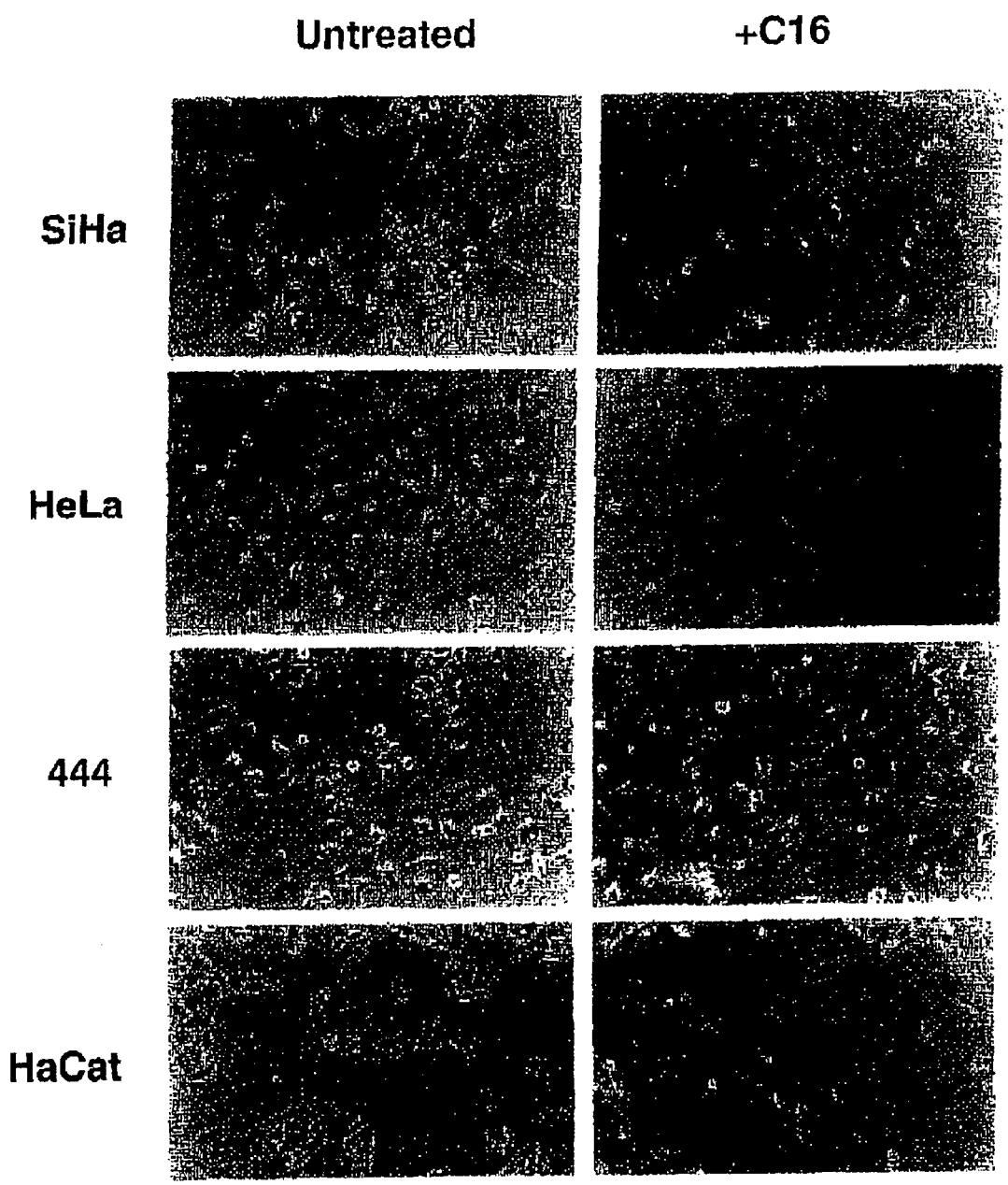
FIG. 4 photographically depicts viability of SiHa, HeLa, 444 and HaCat cells when treated with C16 compound.

Microscopic observation (FIG. 4) demonstrates in addition the differential effect of C16 on E6-dependent cells (SiHa and HeLa) and E6-independent cells (444 and HaCat). Cell viability and the cytotoxic specificity for a number of other compounds of Formula (I) and (II) were also determined. The results are depicted in Table 3.

TABLE 3

| Compound | WST1 | WST1-spec |
|---|---|---|
| DMSO | − | − |
| C16 | + | + |
| C27 | + | − |
| C32 | ++ | |
| C35 | + | − |
| C37 | + | + |
| C38 | + | + |
| C39 | + | + |
| C41 | + | + |
| C42 | + | − |
| C48 | + | + |
| C49 | + | − |
| C55 | + | + |
| C57 | + | + |
| C63 | + | + |
| C65 | + | + |
| C69 | − | − |
| C70 | + | + |
| C71 | + | + |
| C75 | + | + |
| C77 | + | + |
| C82 | + | |
| C83 | + | |
| R24 | + | − |
| R25 | − | − |
| R26 | + | − |

WST1: +: cytotoxic effect in cell culture at 50 µM
WST1-spec +: specific cytotoxic effects of compounds at 50 µM in cell culture for HPV containing cell lines as HeLa, SiHa and Caski, compared to HPV-negative cell lines MCF7, HEPG2, (HaCat, HT3, 444).

EXAMPLE 6

Western Blot Detection of p53 and poly-ADP Ribose Polymerase (PARP)

Figure 5:
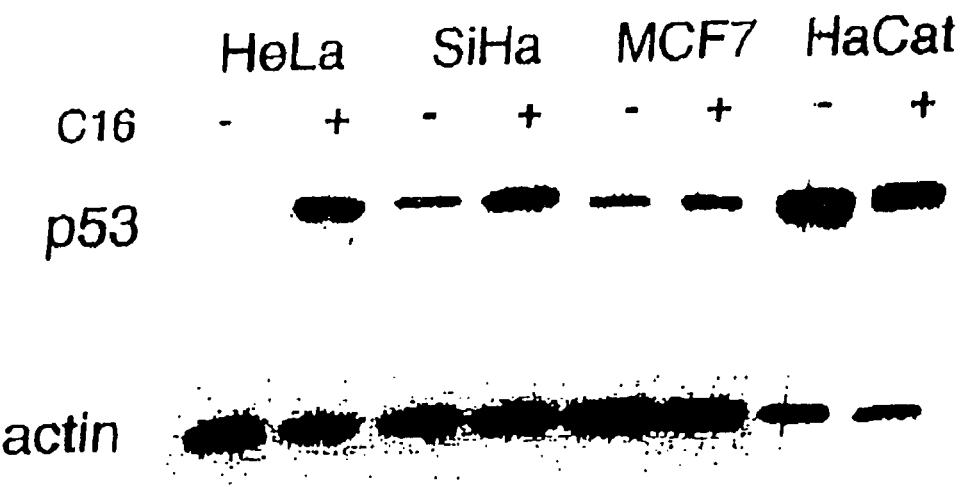
FIG. 5A depicts p53 protein expression for the cell lines HeLa, SiHa, MCF7 and HaCat when treated with C16.
FIG. 5B depicts the cleavage of poly-ADP ribose polymerase (PARP) in HeLa cells incubated with C16 overnight but not C16 treated HaCat cells.
Figure 5:
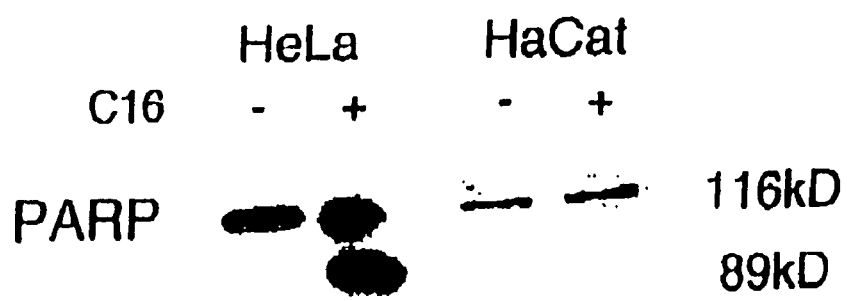

$10^6$ cells were plated on 10 cm petri-dishes with 10 ml medium and after attachment overnight, treated with 100 µM C16 or 0.5% DMSO for one day. At the time of cell harvest most C16-treated cells were still attached to the plate. Cells were harvested using a rubber policeman and lysed in 10 mM Hepes buffer, pH 7.2, 150 mM NaCl, 0.2% Nonidet-P40 (NP40) and 1 mM PMSF, followed by centrifugation. 20 µg of protein was loaded onto a 12% SDS-polyacrylamide gel, transferred to a nitrocellulose membrane and the membrane blocked with 5% nonfat dry milk in 20 mM Tris-Cl, pH 7.6, 150 mM NaCl, 0.05% Tween-20 overnight at 4° C. The membrane was then probed with primary antibodies against p53 (Santa Cruz Biotechnology, Santa Cruz, Calif.), β-actin (Sigma, St. Louis, Mo.) or PARP (C210, Centre de Research du Chul, Quebec, Canada) and followed by incubation with horseradish peroxidase-conjugated secondary antibody (Pierce, Rockford, Ill.). Finally, the blot was treated with an enhanced chemiluminescent detection substrate (SuperSignal, Pierce) and autoradiographed. Results are given in FIG. 5.

The E6 protein forms a heteromeric complex with E6AP and P53 thereby targeting P53 for degradation (30). To examine whether inhibition of E6-E6AP interaction with compounds might influence P53 levels and stability, the effect of C16 on the P53 expression was monitored (FIG. 5A) and quantified with a densitometer.

Increases in P53 expression are known to be associated with programmed cell death (apoptosis) (29), therefore PARP cleavage, a hallmark of apoptosis was examined in C16 treated cells. PARP cleavage was observed in C16 treated HeLa cells but not in HPV-negative HaCat cells which carry a mutant p53 gene (31) (FIG. 5B).

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

BIBLIOGRAPHY

1. Howley, P. M. 1996. Papillomavirinae: The viruses and their replication. p. 947–978. In Field, B. N., Knipe, D. M., and P. M. Howley (eds). Field's Virology, Lippincott Raven Publ. Philadelphia.
2. International Agency for Research on Cancer. IARC Monographys on the evaluation of carcinogenic risks to humans. Volume 64: Human papillomaviurses. 1995, IARC, Lyon, France.
3. Scheffner, M. H. New epidemiology of human papillomavirus infection and cervical neoplasia. J. Natl. Cancer Inst. 87, 1345–1347 (1995).
4. Sherman, L., Jackman, A., Itzhaki, H. Stoppler, M. C., Koval, D., Schlegel R. Inhibition of serum-and calcium-induced differentiation of human keratinocytes by HVP16 E6 oncoprotein: role of p53 inactivation. Virology 237, 296–306 (1997).
5. Chen, J. J., Reid, C. E., Band, V., Androphy, E. J. Interaction of papillomavirus E6 oncoproteins with a putative calcium-binding protein. Science 269, 529–531 (1995).
6. Tong, X and Howley, P. M. The bovine papillomavirus E6 oncoprotein interacts with paxillin and disrupts the actin cytoskeleton. Proc. Natl. Acad. Sci. USA 94, 4412–4417 (1997).
7. Sedman, S. A., Barbosa, M. S., Vass, W. C., Hubbert, N. I., Hass, J. A., Lowy, D. R., Schiller, J. T. The full-length E6 protein of human papillomavirus type 16 has transforming and transactivating activities and cooperates with E7 to immortalize keratinocytes in culture. J. Virol. 65, 48604866 (1991).
8. Lamberti, C., Morrissey, L. C., Grossman, S. R., Androphy, E. J. Transcriptional activation by the papillomavirus E6 zinc finger oncoprotein. EMBO J. 9, 1907–1913 (1990).
9. Etscheid, B. G., Foster, S. A., Galloway, D. A. The E6 protein of human papillomavirus type 16 functions as a transcriptional repressor in a mechanism independent of the tumor suppressor protein p53. Virology 205, 583–585 (1994).
10. Klingelhutz, A. J. Foster, S. A., McDougall, J. K., Telomerase activation by the E6 gene product of human papillomavirus type 16., Nature, 1996, 380: 79–82.
11. Myers, G. and Androphy, E. The E6 protein. p. III-47–III-57. In: Myers, G., Bernard, H. U., Delius, H., Baker, C., Icenogel, J., Halpern, A., Wheeler, C. Human papillomaviruses 1995. Los Alamos National Laboratory, Los Alamos, N. Mex.
12. Grossman, S. R., Laimins, L. A. E6 protein of human papillomavirus type 18 binds zinc. Oncogene 4, 1089–1093 (1989).
13. Kanda, T., Watanabe, S., Zanma, S., Sato, H., Furuno, A., Yoshiike, K. Human papillomavirus type 16 proteins with glycine substitution fo cysteine in the metal-binding motif. Virology 185, 536–543 (1991).
14. Dsouza, M., Larsen, N., Overbeek, R. Searching for patterns in genomic data. Trends in Genetics 13, 497–498 (1997).
15. Chan, S. Y., Delius, H., Halpern, A. L., and Bernard, H. U. Analysis of genomic sequences of 95 papillomavirus types: Uniting typing, phylogeny, and taxonomy. J. Virol. 69, 3074–3083 (1995).
16. Myers, G., Bernard, H. U., Delius, H., Favre, M., Icenogel, J., van Ranst, M., Wheeler, C. Human papillomaviruses 1994. p. II-E6-1–II-E6-7. Los Alamos National Laboratory, Los Alamos, N. Mex.
17. van Ranst, M., Kaplan, J. B., Burk, R. D. Phylogenetic classification of human papillomaviruses: correlation with clinical manifestations. J. Gen. Virol. 73, 2653–2660 (1992).
18. Frederickson, C. J., Kasarskis, E. J., Ringo, D., Frederickson, R. E. A quinoline fluorescence method for visualizing and assaying the histchemically reactive zinc (Bouton zinc) in the brain. J. Neurosci. Meth. 20, 91–103 (1987).
19. Crook, T., Tidy, J. A., Vousden, K. H. Degradation of p53 can be targeted by HPV E6 sequences distinct from those required for p53 binding and transactivation. Cell 67, 547–556 (1991).
20. Dalal, S., Gao, Q., Androphy, E. J., Band, V. Mutational analysis of human papillomavirus type 16 E6 demonstrates that p53 degradation isnecessary for immortalization of mammary epithelial cells. J. Virol. 70, 683–688 (1996).
21. Nakagawa, S., Wantanabe, S., Yoshikawa, H., Taketani, Y., Yoshiike, K., Kanda, T. Mutational analysis of human papillomavirus type 16 E6 protein: Transforming function for human cells and degradation of p53 in vitro. Virology 212, 535–542 (1995).
22. Vousden, K. H., Androphy, E. J., Schiller, J. T., Lowry, D. R. Mutational analysis of bovine papillomavirus type 1 E6 protein, J. Virol. 63, 2340–2342(1989).
23. Bartsch, D., Boye, B., Baust, C., zur Hausen, H. &Schwarz, E. Retinoic acid-mediated repression of human papillomavirus 18 transcription an different ligand regulation of the retinoic acid receptor bega gene in non-tumorigenic and tumorigenic HeLa hybrid cells. EMBO J. 11, 2283–2291 (1992).
24. Bosch, F. X et al. Supression in vivo of human papilloma virus type 18 E6–E7 gene expression in nontumorigenic HeLa x fibroblast hybrid cells. J. Virology 64, 4743–4754 (1990).
25. Tummino, P. J. et al. The in vitro ejection of zinc from human immunodeficiency virus (HIV) type 1 nucleocapsid protein by disulfide benzamides with cellular anti-HIV activity. Proc. Natl. Acad. Sci. USA 93, 969–973.
26. Rice, W. G., Turpin, J. A., Schaeffer, C. A., Graham, L., Clanton, D., Buckheit, R. W., Zaharevitz, D., Summers, M. F., Wallqvist, A., Covell, D. G., Evaluation of selected chemotypoes in coupled cellular and molecular target-based screens identifies novel HIV-1 zinc finger inhibitors. J. Medicinal Cham., 39,3606–3616 (1996).
27. Rice, W. G., Supko. J. G., Malspeis, L., Buckheit, R. W. J., Clanton, D., Bu M. et al, Inhibitors of HIV nucleocapsid protein zinc fingers as candidates for treatment of AIDS, *Science,* 1995; 270; 1194–1197.

28. Huibregtse J. M., Scheffner, M., Howley, P. M. Cloning and expression of the cDNA for E6-AP, a protein that mediates the interaction of the human papillomavirus E6 oncoprotein with p 53. *Mol Cell Biol.* 1993; 13: 775–784.

29. Polyak, K., Xia, Y., Zweier, J. L., Kinzler, K. W., Vogelstein B. A model for p53-induced apoptosis *Nature* 1997; 389:300–305.

30. Scheffner, M., Huibregtse, J. M., Howley, P. M., Identification of a huan ubiquintin-conjugating enzyme that mediates the E6-AP-dependent ubiquitination of p53. Proc Natl. Acad. Sci. U.S.A. 1994; 91:8797–8801.

31. Lehman, T. A., Modali, R., Boukamp, P., Stanek, J., Bennett, W. P., Welsh, J. A., et al. p53 mutations in human immortalized epithelial cell lines (published erratum appears in Carcinogenesis 1993 July: 14(7): 1491) *Carcinogenesis* 1993: 14:833–839.

32. White, A. E., Livanos, E. M., Tlsty, T. D. Differential disruption of genomic integrity and cell cycle regulation in normal human fibroblasts by the HPV oncoproteins. Genes Dev. 1994: 8:666–677.

33. Tan, T. M., Ting, R. C. In vitro and in vivo inhibition of human papillomavirus type 16 E6 and E7 genes. *Cancer Res.* 1995: 55:4599–4605.

34. von Knebel, D., Rittmuller, C., zur HH, Durst, M., Inhibition of tumorigenicity of cervical cancer cells in nude mice by HPV E6–E7 anti-sense RNA (letter). *Int. J. Cancer* 1992: 52: 831–834.

What is claimed is:

1. A method of treating a disease condition caused or exacerbated by an HPV wherein said disease condition is cervical cancer or precursor lesions thereof, asymptomatic infections of the cervix and genital, common, plantar or planar warts, comprising the administration to a mammal in need thereof of an effective amount of a compound which facilitates disruption of a chelated metal cation domain of a protein encoded for by an HPV gene, wherein the compound is selected from the group of compounds consisting of formulae (I):

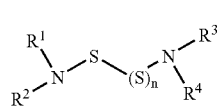
(I)

wherein n is selected from 1–5

$R^1$–$R^4$ are independently selected from the group consisting of hydrogen, optionally substituted alkyl, optionally substituted alkenyl, optionally substituted alkynyl, optionally substituted aryl, optionally substituted arylalkyl optionally substituted acyl, optionally substituted heterocyclyl, halo alkyl, arylalkyl, carboxy, carboxy ester and carboxamido; or $R^1$ and $R^2$ together, and/or $R^3$ and $R^4$ together, independently form a group of formula (a):

(a)

wherein:

U is $CH_2$, O, NH or S;

l and n are independently selected from 0 to 6 and m is 0 or 1 when U is $CH_2$ and m is 1 when U is O, NH or S, such that l+m+n is greater than or equal to 2;

and wherein any one or more ($CH_2$) or NH groups may be further optionally substituted or a pharmaceutically acceptable derivative thereof.

2. A method according to claim 1 wherein $R^1$ and $R^2$ together, and/or $R^3$ and $R^4$ together, independently form a group of formula (a):

(a)

wherein:

U is selected from $CH_2$, O, NH or S;

l and n are independently selected from 0 to 6 and m is 0 or 1 when U is $CH_2$ and m is 1 when U is O, NH or S, such that l+m+n is greater than or equal to 2;

and wherein any one or more ($CH_2$) or NH groups may be further optionally substituted.

3. A method according to claim 2 wherein U is $CH_2$.

4. A method according to claim 3 wherein formula (a) is selected from the group consisting of —$(CH_2)_2$—, —$(CH_2)_3$—, —$(CH_2)_4$—, —$(CH_2)_5$—, —$(CH_2)_6$— and —$(CH_2)_7$—.

5. A method according to claim 2 wherein U is NH, O, or S and m is 1.

6. A method according to claim 2 wherein $R_1$ and $R_2$, and/or $R_3$ and $R_4$, together with the nitrogen to which they are attached independently form a group selected from the group consisting of:

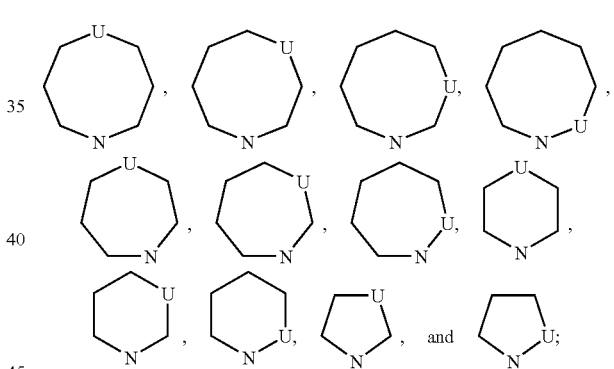

which may be optionally substituted at a carbon atom, and/or where U is NH, at the nitrogen atom.

7. A method according to claim 6 wherein $R_1$ and $R_2$, and/or $R_3$ and $R_4$, together with the nitrogen to which they are attached each independently form an optionally substituted morpholino, thiomorpholino, or piperazino group.

8. A method according to claim 2 wherein any —$CH_2$— group of formula (a) is optionally substituted by one or more of the groups selected from the group consisting of methyl, ethyl, n-propyl, iso-propyl, hydroxy, halo, methoxy, ethoxy, isopropoxy, acetoxy, optionally substituted benzyl, optionally substituted pyridyl, optionally substituted pyrimidyl and optionally substituted phenyl.

9. A method according to claim 1 wherein at least one of $R^1$–$R^4$ is independently selected from the group consisting of: hydrogen, optionally substituted phenyl, optionally substituted cyclopropyl, optionally substituted cyclobutyl, optionally substituted cyclopentyl, and optionally substituted cyclohexyl, formyl, acetyl.

10. A method according to claim 8 wherein the optional substituent is selected from the group consisting of methyl, ethyl, n-propyl, iso-propyl, hydroxy, halo, methoxy, ethoxy, iso-propoxy, acetoxy, and phenyl.

11. A method according to claim 1 wherein at least one of $R^1$–$R^4$ is selected from the group consisting of:

—CH$_2$-Ph,   —CH$_2$—C(O)—O—CH$_2$CH$_3$,   —C(O)H,
—CH$_2$—CH$_3$ and

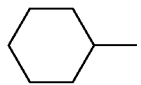

or $R^1$ and $R^2$ together and/or $R^3$ and $R^4$ together independently form a group selected from the group consisting of:

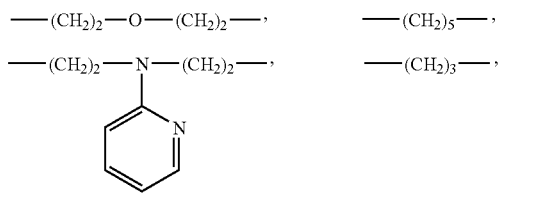

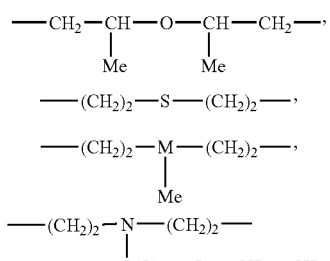

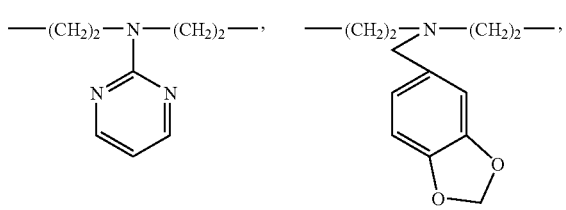

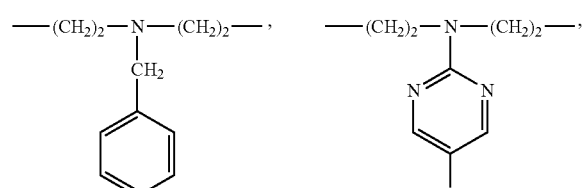

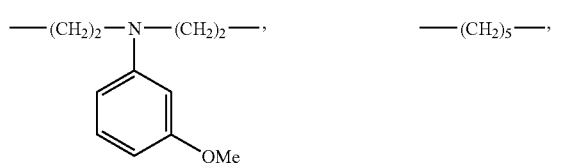

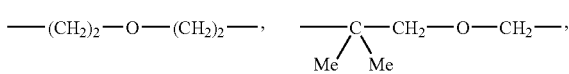

-continued

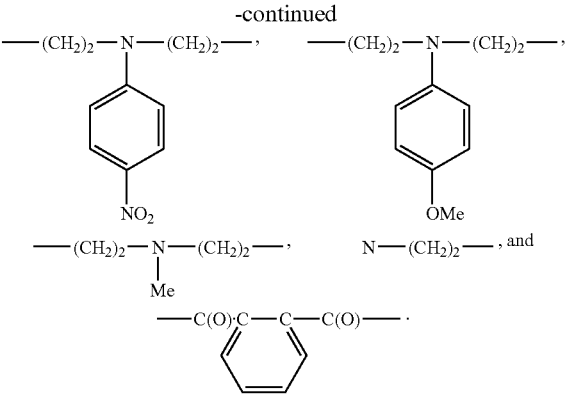

12. A method according to claim 1 wherein n is 1, 2 or 3.

13. A method according to claim 1 wherein the HPV is HPV-16.

14. A method according to claim 13 wherein the protein is the HPV-16 E6 or E7 oncoprotein.

15. A method according to claim 1 wherein the HPV is HPV-18.

16. A method according to claim 15 wherein the protein is the HPV-18 E6 or E7 oncoprotein.

17. A method according to claim 1 where the chelated metal cation domain is a chelated zinc cation domain.

18. A method according to claim 17 wherein the chelated zinc domain is the sequence motif cys-X2-cys-X29-cys-X2-cys (SEQ ID NO:2).

19. A method of treating a disease condition caused or exacerbated by an HPV which is cervical cancer or precursor lesions thereof, asymptomatic infections of the cervix and genital, common, plantar or planar warts comprising the administration of an effective amount of a compound as defined in claim 1 to a mammal in need thereof.

20. A method according to claim 1 wherein the compound is capable of effecting at least 30% zinc release in a TSQ assay and/or inhibits or reduces the binding of an E6 protein to E6AP or E6BP and/or exhibits selective cytotoxicity towards MPV-infected cells.

21. A method according to claim 1 wherein the disease or condition is cervical cancer or its HPV associated precursor lesions.

22. A method of treating a disease condition caused or exacerbated by an HPV and which is cervical cancer or precursor lesions thereof, asymptomatic infections of the cervix and genital, common, plantar or planar warts comprising the administration of an effective amount of a compound capable of facilitating the disruption of a chelated metal cation domain of a protein encoded for by an HPV gene to a mammal in need thereof, wherein said compound is a compound identified as a compound useful in the treatment of a disease or condition caused or exacerbated by an HPV by a method which comprises contacting a protein molecule containing a chelated metal cation domain, encoded by an HPV gene, with an effective amount of said compound for a time and under conditions sufficient to facilitate disruption of the chelated metal cation domain and directly or indirectly determining the amount of chelated metal cation released wherein the amount of chelated metal cation released is indicative of the disruption of the chelated metal cation domain wherein the compound is selected from the group of compounds consisting of formulae (I):

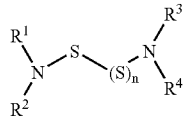 (I)

wherein
n is selected from 1–5
R¹–R⁴ are independently selected from the group consisting of hydrogen, optionally substituted alkyl, optionally substituted alkenyl, optionally substituted alkynyl, optionally substituted aryl, optionally substituted arylalkyl optionally substituted acyl, optionally substituted heterocyclyl, halo alkyl, arylalkyl, carboxy, carboxy ester and carboxamido; or R¹ and R² together, and/or R³ and R⁴ together, independently form a group of formula (a):

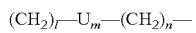 (a)

wherein:
U is $CH_2$, O, NH or S;
l and n are independently selected from 0 to 6 and m is 0 or 1 when U is $CH_2$ and m is 1 when U is O, NH or S, such that l+m+n is greater than or equal to 2;
and wherein any one or more ($CH_2$) or NH groups may be further optionally substituted or a pharmaceutically acceptable derivative thereof.

23. The method according to claim 1 wherein the compound is 4,4-dithiodimorpholine.

24. A method according to claim 1 wherein n is 1 or 2.

* * * * *